US008741890B2

(12) United States Patent
Gerlach et al.

(10) Patent No.: US 8,741,890 B2
(45) Date of Patent: Jun. 3, 2014

(54) SUBSTITUTED AMIDES, MANUFACTURING AND USE THEREOF AS MEDICAMENTS

(75) Inventors: Kai Gerlach, Mittelbiberach (DE); Herbert Nar, Ochsenhausen (DE); Henning Priepke, Warthausen (DE); Annette Schuler-Metz, Ulm (DE); Wolfgang Wienen, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 736 days.

(21) Appl. No.: 12/742,786

(22) PCT Filed: Nov. 14, 2008

(86) PCT No.: PCT/EP2008/065510
§ 371 (c)(1),
(2), (4) Date: Mar. 17, 2011

(87) PCT Pub. No.: WO2009/063028
PCT Pub. Date: May 22, 2009

(65) Prior Publication Data
US 2011/0166125 A1 Jul. 7, 2011

(30) Foreign Application Priority Data
Nov. 15, 2007 (EP) .................................. 07120757

(51) Int. Cl.
C07D 413/14 (2006.01)
A61K 31/55 (2006.01)

(52) U.S. Cl.
USPC ............ 514/212.07; 514/217.01; 514/217.02; 540/523; 540/594; 540/595

(58) Field of Classification Search
USPC ........... 514/212.07, 217.01, 217.02; 540/523, 540/594, 595
See application file for complete search history.

(56) References Cited

U.S. PATENT DOCUMENTS

| 7,157,456 | B2 | 1/2007 | Straub et al. |
| 7,371,743 | B2 | 5/2008 | Priepke et al. |
| 7,476,663 | B2 | 1/2009 | Pfau et al. |
| 7,563,786 | B2 | 7/2009 | Priepke et al. |
| 7,615,549 | B2 | 11/2009 | Gerlach et al. |
| 7,732,466 | B2 | 6/2010 | Pfau et al. |
| 7,947,700 | B2 | 5/2011 | Priepke et al. |
| 8,309,542 | B2 | 11/2012 | Gerlach et al. |
| 8,445,525 | B2 | 5/2013 | Priepke et al. |
| 2005/0064006 | A1 | 3/2005 | Perzborn et al. |
| 2005/0256107 | A1 | 11/2005 | Pfau et al. |
| 2005/0272792 | A1 | 12/2005 | Gerlach et al. |
| 2006/0148883 | A1 | 7/2006 | Park et al. |
| 2007/0032473 | A1 | 2/2007 | Gerlach et al. |
| 2008/0015178 | A1 | 1/2008 | Gerlach et al. |
| 2008/0051578 | A1 | 2/2008 | Dahmann et al. |
| 2008/0306070 | A1 | 12/2008 | Perzborn et al. |
| 2010/0216769 | A1 | 8/2010 | Priepke et al. |
| 2010/0317848 | A1 | 12/2010 | Han et al. |
| 2012/0004202 | A1 | 1/2012 | Park et al. |
| 2013/0005962 | A1 | 1/2013 | Han et al. |
| 2013/0237522 | A1 | 9/2013 | Priepke et al. |

FOREIGN PATENT DOCUMENTS

| CA | 2 464 290 A1 | 5/2003 |
| CA | 2565698 A1 | 12/2005 |
| CA | 2581580 A1 | 4/2006 |
| CA | 2591089 A1 | 6/2006 |
| CA | 2 615 447 A1 | 1/2007 |
| CA | 2 624 310 A1 | 4/2007 |
| CA | 2 624 323 A1 | 4/2007 |
| CA | 2641912 A1 | 8/2007 |
| CA | 2653753 A1 | 11/2007 |
| WO | 0147919 A1 | 7/2001 |
| WO | 03/035133 A1 | 5/2003 |
| WO | 2004056784 A1 | 7/2004 |
| WO | 2004058743 A1 | 7/2004 |
| WO | 2005082895 A1 | 9/2005 |
| WO | 2005111013 A1 | 11/2005 |
| WO | 2005111014 A1 | 11/2005 |
| WO | 2005111029 A1 | 11/2005 |
| WO | 2005121103 A1 | 12/2005 |
| WO | 2006034822 A1 | 4/2006 |
| WO | 2006069946 A1 | 7/2006 |
| WO | 2006089909 A1 | 8/2006 |
| WO | 2007/009963 A1 | 1/2007 |
| WO | 2007003536 A1 | 1/2007 |
| WO | 2007025940 A1 | 3/2007 |
| WO | 2007/039132 A1 | 4/2007 |
| WO | 2007/039134 A1 | 4/2007 |
| WO | 2007093595 A1 | 8/2007 |
| WO | 2007131982 A2 | 11/2007 |
| WO | 2008080891 A2 | 7/2008 |
| WO | 2008116881 A1 | 10/2008 |
| WO | 2008135524 A2 | 11/2008 |
| WO | 2008135525 A2 | 11/2008 |
| WO | 2008135526 A1 | 11/2008 |

OTHER PUBLICATIONS

International Search Report for PCT/EP2008/065510 mailed Jul. 13, 2008.

Primary Examiner — Brenda Coleman
(74) Attorney, Agent, or Firm — Michael P. Morris; Edouard G. Lebel; Usha R. Patel

(57) ABSTRACT

The present invention relates to new substituted prolinamides of general formula (I) wherein D, Y, A, B, $R^3$, $R^4$ and $R^5$ are defined as in the specification, the tautomers, the enantiomers, the diastereomers, the mixtures thereof and the salts thereof, particularly the physiologically acceptable salts thereof with inorganic or organic acids or bases, which have valuable properties.

(I)

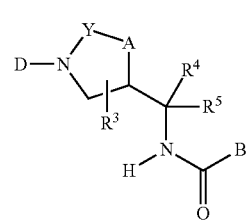

5 Claims, No Drawings

SUBSTITUTED AMIDES, MANUFACTURING AND USE THEREOF AS MEDICAMENTS

This application is the national phase entry under 35 U.S.C. §371 of International Application No. PCT/EP2008/065510, filed Nov. 14, 2008, which claims priority to European Patent Application No. 07120757.5, filed Nov. 15, 2007, which are hereby incorporated by reference in their entireties.

The present invention relates to new substituted amides of general formula (I)

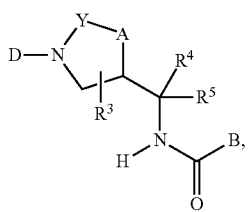

(I)

the tautomers, the enantiomers, the diastereomers, the mixtures thereof and the salts thereof, particularly the physiologically acceptable salts thereof with inorganic or organic acids or bases, which have valuable properties.

The compounds of the above general formula I as well as the tautomers, the enantiomers, the diastereomers, the mixtures thereof and the salts thereof, particularly the physiologically acceptable salts thereof with inorganic or organic acids or bases, and the stereoisomers thereof have valuable pharmacological properties, particularly an antithrombotic activity and a factor Xa-inhibiting activity.

The present application relates to new compounds of the above general formula I, the preparation thereof, the pharmaceutical compositions containing the pharmacologically effective compounds, the preparation and use thereof.

A first embodiment of the present invention encompasses those compounds of general formula I wherein
D denotes a substituted bicyclic ring system of formula (II)

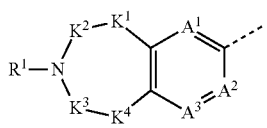

(II)

wherein $K^1$ and $K^4$
each independently of one another denote a bond, a —$CH_2$—, —$CHR^{2a}$—, —$CR^{2b}R^{2b}$— or a —C(O)— group, and wherein
$R^{2a}/R^{2b}/R^{2c}$
each independently of one another denote a fluorine atom, a hydroxy, $C_{1-5}$-alkyloxy, amino, $C_{1-5}$-alkylamino, di-($C_{1-5}$-alkyl)-amino, $C_{3-5}$-cycloalkyleneimino, $C_{1-5}$-alkylcarbonylamino group, a $C_{1-5}$-alkyl group which may be substituted by 1-3 fluorine atoms, a hydroxy-$C_{1-5}$-alkyl, $C_{1-5}$-alkyloxy-$C_{1-5}$-alkyl, amino-$C_{1-5}$-alkyl, $C_{1-5}$-alkylamino-$C_{1-5}$-alkyl, di-($C_{1-5}$-alkyl)-amino-$C_{1-5}$-alkyl, $C_{4-7}$-cycloalkyleneimino-$C_{1-5}$-alkyl, carboxy-$C_{0-5}$-alkyl, $C_{1-5}$-alkyloxycarbonyl-$C_{0-5}$-alkyl, aminocarbonyl-$C_{0-5}$-alkyl, $C_{1-5}$-alkylaminocarbonyl-$C_{0-5}$-alkyl, di-($C_{1-5}$-alkyl)-aminocarbonyl-$C_{0-5}$-alkyl or a $C_{4-7}$-cycloalkyleneiminocarbonyl-$C_{0-5}$-alkyl group,
while the two groups $R^{2b}/R^{2c}$ cannot both simultaneously be bound to the cyclic carbon atom via a heteroatom, except where —$C(R^{2b}R^{2b})$— corresponds to a —$CF_2$ group, or
$R^{2a}$ denotes a phenyl or monocyclic heteroaryl group substituted by fluorine, chlorine, bromine, methyl, methoxy, amino or nitrogen, or
two groups $R^{2b}/R^{2c}$ together with the cyclic carbon atom may form a 3-, 4-, 5-, 6- or 7-membered saturated carbocyclic group or a cyclopentene, cyclohexene, oxetane, azetidine, thietane, tetrahydrofuran, pyrrolidine, tetrahydrothiophene, tetrahydropyran, piperidine, pentamethylene sulphide, hexamethyleneimine, 1,3-dioxolane, 1,4-dioxane, hexahydropyridazine, piperazine, thiomorpholine, morpholine, 2-imidazolidinone, 2-oxazolidinone, tetrahydro-2(1H)-pyrimidinone or [1,3]oxazinan-2-one ring,
while the methylene groups thereof may be substituted by 1-2 $C_{1-3}$-alkyl or $CF_3$— groups, and/or
the methylene groups thereof, if they are not bound to a heteroatom, may be substituted by 1-2 fluorine atoms, and/or
wherein a —$CH_2$ group besides an N atom may be replaced by a —CO group, and/or
the imino groups of which may each be substituted by a $C_{1-3}$-alkyl or $C_{1-3}$-alkylcarbonyl group, and/or
wherein the sulphur atom may be oxidised to a sulphoxide or sulphone group,
$K^2$ and $K^3$
each independently of one another denote a —$CH_2$, —$CHR^{6a}$, —$CR^{6b}R^{6c}$ or a —C(O) group, wherein $R^{6a}/R^{6b}/R^{6c}$
each independently of one another denote a $C_{1-5}$-alkyl group which may be substituted by 1-3 fluorine atoms, a hydroxy-$C_{1-5}$-alkyl, $C_{1-5}$-alkyloxy-$C_{1-5}$-alkyl, amino-$C_{1-5}$-alkyl, $C_{1-5}$-alkylamino-$C_{1-5}$-alkyl, di-($C_{1-5}$-alkyl)-amino-$C_{1-5}$-alkyl, $C_{4-7}$-cycloalkyleneimino-$C_{1-5}$-alkyl, carboxy-$C_{0-5}$-alkyl, $C_{1-5}$-alkyloxycarbonyl-$C_{0-5}$-alkyl, aminocarbonyl-$C_{0-5}$-alkyl, $C_{1-5}$-alkylaminocarbonyl-$C_{0-5}$-alkyl, di-($C_{1-5}$-alkyl)-aminocarbonyl-$C_{0-5}$-alkyl or a $C_{4-7}$-cycloalkyleneiminocarbonyl-$C_{0-5}$-alkyl group,
or two groups $R^{6b}/R^{6c}$ together with the cyclic carbon atom may form a 3-, 4-, 5-, 6- or 7-membered saturated carbocyclic group or a cyclopentene, cyclohexene, oxetane, azetidine, thietane, tetrahydrofuran, pyrrolidine, tetrahydrothiophene, tetrahydropyran, piperidine, pentamethylene sulphide, hexamethyleneimine, hexahydropyridazine, tetrahydro-2(1H)-pyrimidinone, [1,3]oxazinan-2-one ring,
while the methylene groups thereof may be substituted by 1-2 $C_{1-3}$-alkyl or $CF_3$— groups, and/or
the methylene groups thereof, if they are not bound to a heteroatom, may be substituted by 1-2 fluorine atoms, and/or
wherein a —$CH_2$ group besides a nitrogen atom may be replaced by a —CO group, and/or
the imino groups of which may each be substituted by a $C_{1-3}$-alkyl or $C_{1-3}$-alkylcarbonyl group, and/or
wherein the sulphur atom may be oxidised to a sulphoxide or sulphone group,
with the proviso that a heteroatom introduced by $R^{6b}$ or $R^{6c}$ cannot be only one carbon atom away from the cyclic nitrogen —$N(R^1)$— in formula (I), and in total in formula (II) a maximum of four groups selected from $R^{2a}$, $R^{2b}$, $R^{2c}$, $R^{6a}$, $R^{6b}$ and $R^{6c}$ may be present, and $R^1$ denotes a hydrogen atom or a hydroxy, $C_{1-3}$-alkyloxy, amino, $C_{1-3}$-alkylamino, di-($C_{1-3}$-alkyl)-amino, a $C_{1-5}$-alkyl, $C_{2-5}$-alkenyl-$CH_2$, $C_{2-5}$-alkynyl-$CH_2$, $C_{3-6}$-cycloalkyl, $C_{4-6}$-cycloalkenyl, oxetan-3-yl, tetrahydrofuran-3-yl, benzyl, $C_{1-5}$-alkyl-carbonyl, trifluoromethyl carbonyl, $C_{3-6}$-cycloalkyl-carbonyl, $C_{1-5}$-alkyl-sulphonyl, $C_{3-6}$-cycloalkyl-sulphonyl, aminocarbonyl, $C_{1-5}$-alkylaminocarbonyl, di-($C_{1-5}$-alkyl)aminocarbonyl, $C_{1-5}$-alkyloxycarbonyl, $C_{4-7}$-cycloalkyleneiminocarbonyl group, while the methylene and methyl groups contained in the groups mentioned previously may additionally be substituted by a $C_{1-3}$-alkyl, carboxy, $C_{1-5}$-alkoxycarbonyl group, or by a hydroxy, $C_{1-5}$-alkyloxy, amino, $C_{1-5}$-alkylamino, $C_{1-5}$-dialkylamino or $C_{4-7}$-cycloalkyleneimino group, provided that the methylene or methyl groups are not directly bound to a heteroatom selected from among O, N or S, and/or one to three hydrogen atoms may be replaced by fluorine atoms, provided that the methylene or methyl groups are not directly bound to a heteroatom selected from among O, N or S, and wherein $A^1$ denotes either N or $CR^9$, $A^2$ denotes either N or $CR^{10}$, $A^3$ denotes either N or $CR^{11}$, while $R^9$, $R^{10}$ and $R^{11}$ each independently of one another denote a hydrogen, fluorine, chlorine, bromine or iodine atom, or a phenyl, $C_{1-5}$-alkyl, $CF_3$, $C_{2-5}$-alkenyl, $C_{2-5}$-alkynyl, a cyano, carboxy, $C_{1-5}$-alkyloxycarbonyl, hydroxy, $C_{1-3}$-alkyloxy, $CF_3O$, $CHF_2O$, $CH_2FO$, amino, $C_{1-5}$-alkylamino, di-($C_{1-5}$-alkyl)-amino or $C_{4-7}$-cycloalkyleneimino group, and $R^3$ denotes a hydrogen atom or a $C_{1-3}$-alkyl group, $R^4$ and $R^5$ each independently of one another denote a hydrogen atom or a straight-chain or branched $C_{1-5}$-alkyl group, which may be wholly or partly substituted by fluorine atoms, and which may optionally be substituted by a hydroxy, $C_{1-4}$-alkyloxy group, a $C_{1-4}$-alkylsulphanyl, or a $C_{1-4}$-alkylsulphonyl group, Y denotes a group of formula

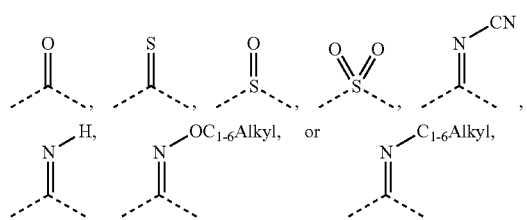

A denotes an oxygen atom or a —N($R^6$)— group, $R^6$ denotes a hydrogen atom or a straight-chain or branched $C_{1-5}$-alkyl group, which may be wholly or partly substituted by fluorine atoms, and which may optionally be substituted by a hydroxy, $C_{1-4}$-alkyloxy group, a $C_{1-4}$-alkylsulphanyl, or a $C_{1-4}$-alkylsulphonyl group, while the heteroatoms O or S optionally introduced as substituents are not separated by precisely one carbon atom from the nitrogen atom substituted by $R^6$ in the heterocyclic group, B denotes a thiophene ring according to formula (III),

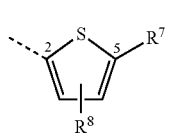

(III)

which is bound to the carbonyl group in formula (I) via the 2 position and which is substituted in the 5 position by $R^7$ and optionally additionally substituted by $R^8$, where $R^7$ denotes a fluorine, chlorine, bromine or iodine atom, or a methoxy, $C_{1-2}$-alkyl or ethynyl group, $R^8$ denotes a hydrogen, fluorine, chlorine, bromine or iodine atom, or a $C_{1-2}$-alkyl or amino group, while, unless stated otherwise, by the term "heteroaryl group" mentioned in the definitions hereinbefore is meant a monocyclic 5- or 6-membered heteroaryl group wherein the 6-membered heteroaryl group contains one, two or three nitrogen atoms, and the 5-membered heteroaryl group contains an imino group optionally substituted according to the above description, or an oxygen or sulphur atom, or an imino group optionally substituted according to the above description or an oxygen or sulphur atom and additionally one or two nitrogen atoms, or an imino group optionally substituted according to the above description and three nitrogen atoms, and furthermore, unless stated otherwise, a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the abovementioned monocyclic heteroaryl groups via two adjacent carbon atoms, and the bond is provided in each case via a nitrogen atom or via a carbon atom of the heterocyclic moiety or a fused-on phenyl ring, while, unless stated otherwise, by the term "halogen atom" mentioned hereinbefore in the definitions is meant an atom selected from among fluorine, chlorine, bromine and iodine, while unless stated otherwise the alkyl, alkenyl, alkynyl and alkoxy groups contained in the definitions mentioned previously which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions, unless stated otherwise, may be wholly or partly replaced by fluorine atoms, the tautomers, the enantiomers, the diastereomers, the mixtures thereof and the salts thereof.

Within the scope of the present application, unless otherwise defined, the following general terms mentioned in the definitions are defined as shown below or illustrated by examples.

Examples of the monocyclic heteroaryl groups mentioned hereinbefore in the definitions are the pyridyl, N-oxy-pyridyl, pyrazolyl, pyridazinyl, pyrimidinyl, pyrazinyl, [1,2,3]triazinyl, [1,3,5]triazinyl, [1,2,4]triazinyl, pyrrolyl, imidazolyl, [1,2,4]triazolyl, [1,2,3]triazolyl, tetrazolyl, furanyl, isoxazolyl, oxazolyl, [1,2,3]oxadiazolyl, [1,2,4]oxadiazolyl, furazanyl, thiophenyl, thiazolyl, isothiazolyl, [1,2,3]thiadiazolyl, [1,3,4]thiadiazolyl or [1,2,5]thiadiazolyl group.

Examples of the bicyclic heteroaryl groups mentioned hereinbefore in the definitions are the benzimidazolyl, benzofuranyl, benzo[c]furanyl, benzothiophenyl, benzo[c]thiophenyl, benzothiazolyl, benzo[c]isothiazolyl, benzo[d]isothiazolyl, benzoxazolyl, benzo[c]isoxazolyl, benzo[d]isoxazolyl, benzo[1,2,5]oxadiazolyl, benzo[1,2,5]thiadiazolyl, benzo[1,2,3]thiadiazolyl, benzo[d][1,2,3]triazinyl, benzo[1,2,4]triazinyl, benzotriazolyl, cinnolinyl, quinolinyl, N-oxy-quinolinyl, isoquinolinyl, quinazolinyl, N-oxy-quinazolinyl, quinoxalinyl, phthalazinyl, indolyl, isoindolyl or 1-oxa-2,3-diaza-indenyl group.

Examples of the $C_{1-5}$-alkyl groups mentioned hereinbefore in the definitions are the methyl, ethyl, 1-propyl, 2-propyl, n-butyl, sec-butyl, tert-butyl, 1-pentyl, 2-pentyl, 3-pentyl, neo-pentyl or 3-methyl-2-butyl group.

Examples of the $C_{1-5}$-alkyloxy groups mentioned hereinbefore in the definitions are the methyloxy, ethyloxy, 1-propyloxy, 2-propyloxy, n-butyloxy, sec-butyloxy, tert-butyloxy, 1-pentyloxy, 2-pentyloxy, 3-pentyloxy or neo-pentyloxy group.

Examples of the $C_{2-5}$-alkenyl groups mentioned hereinbefore in the definitions are the ethenyl, 1-propen-1-yl, 2-propen-1-yl, 1-buten-1-yl, 2-buten-1-yl, 3-buten-1-yl, 1-penten-1-yl, 2-penten-1-yl, 3-penten-1-yl, 4-penten-1-yl, 1-hexen-1-yl, 2-hexen-1-yl, 3-hexen-1-yl, 4-hexen-1-yl, 5-hexen-1-yl, but-1-en-2-yl, but-2-en-2-yl, but-1-en-3-yl, 2-methyl-prop-2-en-1-yl, pent-1-en-2-yl, pent-2-en-2-yl, pent-3-en-2-yl, pent-4-en-2-yl, pent-1-en-3-yl, pent-2-en-3-yl, 2-methyl-but-1-en-1-yl, 2-methyl-but-2-en-1-yl, 2-methyl-but-3-en-1-yl or 2-ethyl-prop-2-en-1-yl group, Examples of the $C_{2-5}$-alkynyl groups mentioned hereinbefore in the definitions are the ethynyl, 1-propynyl, 2-propynyl, 1-butyn-1-yl, 1-butyn-3-yl, 2-butyn-1-yl, 3-butyn-1-yl, 1-pentyn-1-yl, 1-pentyn-3-yl, 1-pentyn-4-yl, 2-pentyn-1-yl, 2-pentyn-3-yl, 3-pentyn-1-yl, 4-pentyn-1-yl, 2-methyl-1-butyn-4-yl, 3-methyl-1-butyn-1-yl or 3-methyl-1-butyn-3-yl group.

A 2nd embodiment of the present invention includes those compounds of general formula (I), wherein D, $R^3$, $R^4$, $R^5$ and B are defined as described in embodiment 1, and wherein Y denotes a group of formula A denotes an oxygen atom.

A 3rd embodiment of the present invention includes those compounds of general formula (I) wherein D, $R^3$, $R^4$, $R^5$ and B are defined as described in embodiment 1 or 2, and wherein Y denotes a carbonyl group, and
A denotes an oxygen atom.

A 4th embodiment of the present invention includes those compounds of general formula (I) wherein Y, A, $R^3$, $R^4$, $R^5$ and B are defined as described in embodiment 1, 2 or 3, and wherein
D denotes a substituted bicyclic ring system of formula (II)

wherein
$K^1$ and $K^4$
each independently of one another denote a bond, a —$CH_2$—, —$CHR^{2a}$— or a —$CR^{2b}R^{2c}$ group, and wherein
$R^{2a}/R^{2b}/R^{2c}$
each independently of one another denote a fluorine atom, a methoxy or a methyl group, or
two groups $R^{2b}/R^{2c}$ together with the cyclic carbon atom may form a cyclopropyl ring, and
$K^2$ and $K^3$
each independently of one another denote a —$CH_2$—, —$CHR^{6a}$ or —$CR^{6b}R^{6c}$— group, wherein
$R^{6a}/R^{6b}/R^{6c}$
each independently of one another denote a methyl group, a $CF_3$ or a cyano group,
or two groups $R^{6b}/R^{6c}$ together with the cyclic carbon atom may form a cyclopropyl ring, and
$R^1$ denotes a hydrogen atom or a $C_{1-3}$-alkyl, or $C_{3-6}$-cycloalkyl group, and
$A^1$ denotes $CR^9$,
$A^2$ denotes $CR^{10}$,
$A^3$ denotes $CR^{11}$,
while $R^9$, $R^{10}$ and $R^{11}$ each independently of one another denote
a hydrogen, fluorine or chlorine atom, or a methyl, $CF_3$, cyano, methoxy, $CF_3O$, $CHF_2O$, $CH_2FO$— group.

A 5th embodiment of the present invention includes those compounds of general formula (I), wherein
D denotes a substituted bicyclic ring system of formula (II)

wherein
$K^1$ and $K^4$
each independently of one another denote a bond, a —$CH_2$, —$CHR^{2a}$— or a —$CR^{2b}R^{2c}$ group represent, and wherein
$R^{2a}/R^{2b}/R^{2c}$
each independently of one another denote a methyl group, or two groups $R^{2b}/R^{2c}$ together with the cyclic carbon atom may form a cyclopropyl ring, and
$K^2$ and $K^3$
each independently of one another denote a —$CH_2$, —$CHR^{6a}$ or —$CR^{6b}R^{6c}$— group, wherein
$R^{6a}/R^{6b}/R^{6c}$
each independently of one another denote a methyl group,
or two groups $R^{6b}/R^{6c}$ together with the cyclic carbon atom may form a cyclopropyl ring, and
$R^1$ denotes a hydrogen atom or a $C_{1-3}$-alkyl, or $C_{3-6}$-cycloalkyl group, and
$A^1$ denotes $CR^9$,
$A^2$ denotes $CR^{19}$,
$A^3$ denotes $CR^{11}$,
while $R^9$, $R^{19}$ and $R^{11}$ each independently of one another denote
a hydrogen, fluorine or chlorine atom, or a methyl, $CF_3$, cyano, methoxy, $CF_3O$, $CHF_2O$, $CH_2FO$— group, and Y denotes a carbonyl group, and
A denotes an oxygen atom, and
$R^3$, $R^4$ and $R^5$ each represent a hydrogen atom, and
B denotes a thiophene ring according to formula (III),

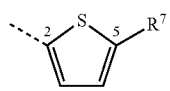
(III)

which is bound to the carbonyl group in formula (I) via the 2 position and which is substituted in the 5 position by $R^7$, where $R^7$ denotes a chlorine or bromine atom, or an ethynyl group.

The invention also relates to physiologically acceptable salts of the compounds according to the embodiments defined hereinbefore and the Examples.

The invention also relates to medicaments, containing a compound or a physiologically acceptable salt of a compound according to the embodiments defined hereinbefore and the Examples, optionally together with one or more inert carriers and/or diluents.

The invention also relates to the use of a compound or a physiologically acceptable salt of a compound according to the embodiments defined hereinbefore and the Examples, for preparing a pharmaceutical composition with a inhibitory effect on factor Xa and/or an inhibitory effect on related serine proteases.

The invention also relates to a process for preparing a pharmaceutical composition, characterised in that a compound or a physiologically acceptable salt of a compound according to the embodiments defined hereinbefore and the Examples is incorporated in one or more inert carriers and/or diluents by a non-chemical method.

According to the invention the compounds of general formula (I) are obtained by methods known per se, for example by the following methods:

(a) The preparation of a compound of general formula (I) wherein D, Y, A, $R^3$, $R^4$, $R^5$ and B are defined as mentioned in embodiment 1 and which may optionally be protected at any amino, hydroxy, carboxy or thiol groups by common protective groups such as for example those described in T. W. Greene, P. G. M. Wuts in "Protective Groups in Organic Synthesis", Wiley, 1991 and 1999, and the protective groups of which may be cleaved by methods known from the literature, is described in the examples or may be carried out for example according to formula scheme 1 or analogously to the methods of synthesis described in WO2002/059115, WO2004/101557 or in WO2006/111285.

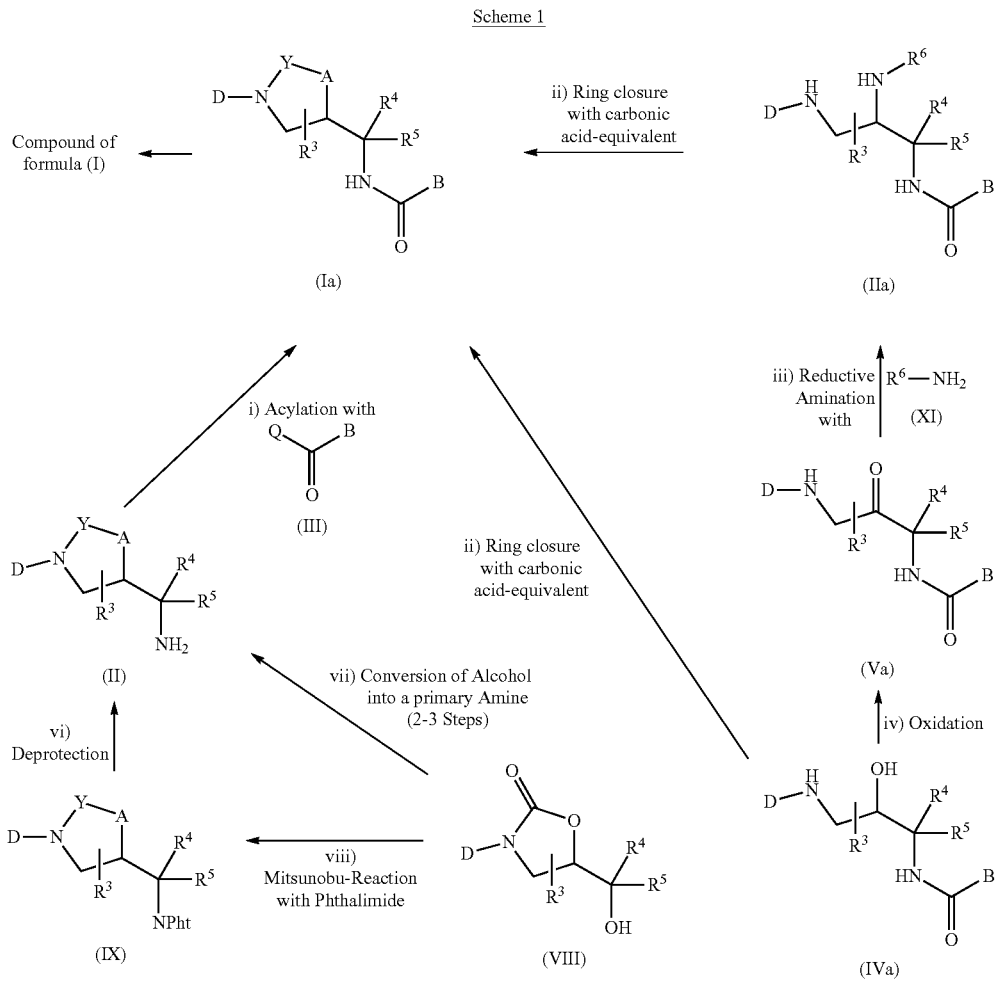
Scheme 1

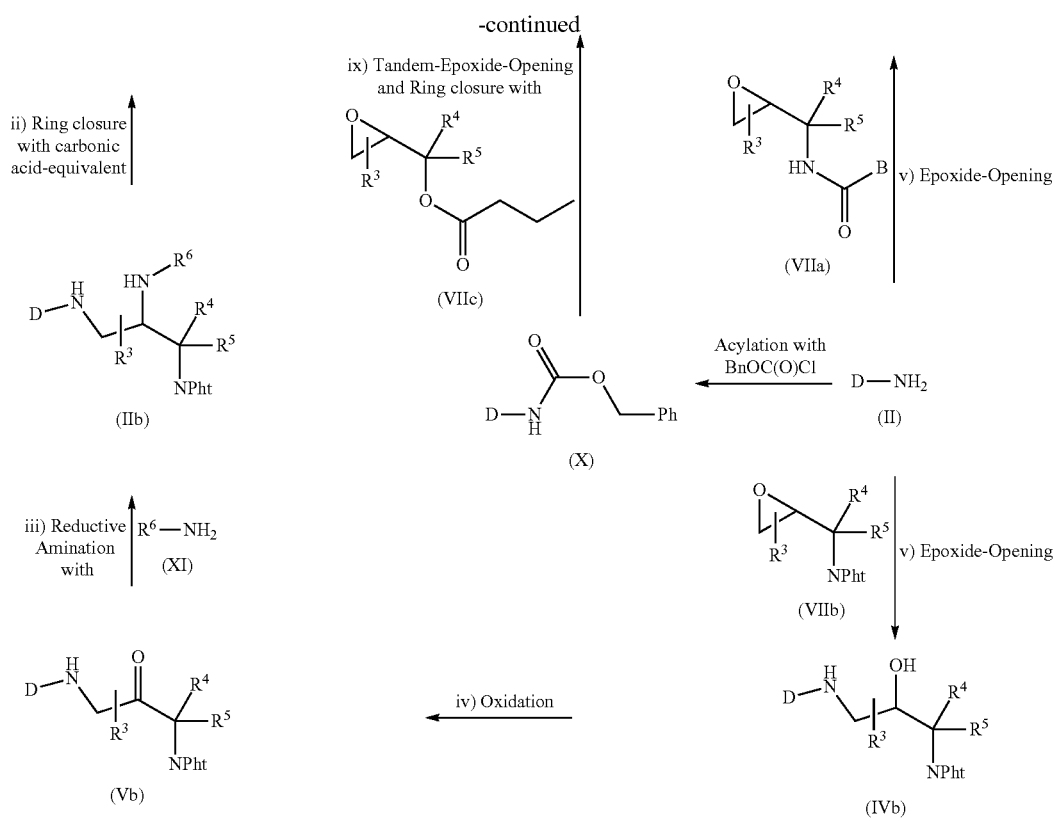

In Scheme 1

Q denotes a hydroxy or $C_{1-4}$-alkoxy group, a halogen atom or an alkoxycarbonyloxy or acyloxy group and Pht denotes a protective group for the amino function known from the literature, such as for example a phthalimide group.

The reaction steps i)-x) described in the Scheme may be carried out as described in the Examples or under conditions known from the literature, for example as follows:

i) by acylating an amine (II) with an optionally activated carboxylic acid (III):

The acylation is conveniently carried out with a corresponding halide or anhydride in a solvent such as methylene chloride, chloroform, carbon tetrachloride, ether, tetrahydrofuran, dioxane, benzene, toluene, acetonitrile, dimethylformamide or sulpholane, optionally in the presence of an inorganic or organic base at temperatures between −20 and 200° C., but preferably at temperatures between −10 and 160° C.

The acylation may however also be carried out with the free acid, optionally in the presence of an acid-activating agent or a dehydrating agent, for example in the presence of isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/camphorsulphonic acid, N,N'-dicyclohexylcarbodiimide/N-hydroxysuccinimide or 1-hydroxybenzotriazole, N,N'-carbonyldiimidazole, O-(benzotriazol-1-yl)-N,N,N',N'-tetramethyl-uronium tetrafluoroborate/N-methylmorpholine, O-(benzotriazol-1-yl)-N,N,N',N'-tetramethyl-uronium tetrafluoroborate/N-ethyldiisopropylamine, O-pentafluorophenyl-N,N,N',N'-tetramethyluronium-hexafluorophosphate/triethylamine, N,N'-thionyldiimidazole or triphenylphosphine/carbon tetrachloride, at temperatures between −20 and 200° C., but preferably at temperatures between −10 and 160° C.

ii) by cyclising an aminoalcohol (IVa) or a diamine (IIa) or (IIb) with a carbonic acid equivalent or a sulphinic acid equivalent optionally followed by oxidation.

The cyclisations are conveniently carried out in a solvent such as methylene chloride, chloroform, carbon tetrachloride, ether, tetrahydrofuran, dioxane, benzene, toluene, acetonitrile, dimethylformamide, sodium hydroxide solution or sulpholane, optionally in the presence of an inorganic or organic base at temperatures between −20 and 200° C., but preferably at temperatures between −10 and 160° C.

The carbonic acid equivalents may be, for example, N,N'-carbonyldiimidazole (CDI), N,N'-carbonylditriazole (CDT), phosgene, diphosgene, triphosgene, dimethyl carbonate or bromocyanogen or N,N'-thiocarbonyldiimidazole in the presence of 4-N,N-dimethylaminopyridine (DMAP).

The sulphinic acid equivalent used may be for example thionyl chloride for synthesising oxazolidinethiones or imidazolidinethiones (Ia) or (IX). The resulting oxazolidinethione or imidazolidinethione (Ia) or (IX) may then be carried out with an oxidising agent such as for example sodium periodate in the presence of ruthenium(III)chloride hydrate in a solvent such as for example acetonitrile in a temperature range from −50° C. to +100° C., but preferably at temperatures between 0° C. and ambient temperature.

iii) by reductive amination of a ketone (Va) or (Vb) with an amine (XI)

The reductive amination of the ketone (Va) or (Vb) with the amine (XI) is conveniently carried out in a solvent or mixture of solvents such as methanol, ethanol, propanol, isopropanol, butanol, tetrahydrofuran, dioxane, diethyl ether, tert.-butylmethyl-ether, ethyleneglycoldimethylether, diethyleneglycol dimethylether, sulpholane, dimethylformamide, N-methylpyrrolidinone, tetraline, dimethylsulphoxide, methylene chloride, chloroform or tetrachloromethane, for example at temperatures between −30 and 250° C., but preferably between −10 and 150° C., optionally in the presence of a base such as sodium methoxide, sodium ethoxide, sodium-tert.-butoxide, potassium-tert.-butoxide, sodium-tert.-butyldimethyl-silanoate, potassium hexamethyldisilazane, lithium diisopropylamide, potassium carbonate, rubidium carbonate, caesium carbonate, potassium phosphate, sodium hydride, optionally in the presence of a complexing agent such as 18-crown-6-ether, followed by reduction of the imine thus formed by hydrogenation with hydrogen, for example at a pressure between 0.5 and 100 bar, but preferably between 1 and 50 bar, conveniently in the presence of a catalyst such as for example Raney nickel, palladium charcoal, platinum oxide, platinum on mineral fibres or rhodium, or with complex hydrides such as lithium aluminium hydride, sodium borohydride, sodium cyanoborohydride, sodium triacetoxyborohydride, diisobutylaluminium hydride, for example at temperatures between −30 and 250° C., but preferably between 0 and 150° C.

iv) by oxidation of an alcohol (IVa) or (IVb) to form ketones (Va) or (Vb)

The oxidation of the alcohol function to form the corresponding ketone is conveniently carried out in a solvent or mixture of solvents such as dichloromethane, chloroform, tetrachloromethane, dimethylsulphoxide, dimethylformamide, for example at temperatures between −100° C. and 100° C., but preferably between −100° C. and 50° C., under conditions of Swern oxidation with dimethylsulphoxide and oxalyl chloride or using analogous methods based on activated dimethylsulphoxide.

v) by nucleophilic ring-opening of the epoxides (VIIa) or (VIIb) with the amine (II) to form aminoalcohols (IVa) or (IVb)

The nucleophilic ring-opening of the epoxides to form the corresponding aminoalcohols is conveniently carried out in a solvent or mixture of solvents such as 1,4-dioxane, ethanol, acetonitrile, tetrahydrofuran or water, for example at temperatures between −100° C. and 150° C., but preferably between −80° C. and 100° C., optionally catalysed by lanthanoid salts such as for example ytterbium(III)trifluoromethanesulphonate.

vi) by cleaving a protective group in Scheme 1:

The optional subsequent cleaving of any protective group used is carried out for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved hydrogenolytically, for example, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, preferably, however, 1 to 5 bar.

A phthalimide group is cleaved in a solvent or mixture of solvents such as methanol, ethanol, isopropanol, water, tetrahydrofuran, 1,4-dioxane, dimethylformamide, for example at temperatures between −100° C. to 150° C., but preferably at temperatures between 0° C. and 100° C., for example with hydrazine hydrate or methylamine.

However, a protective group may also be cleaved by the methods described by T. W. Greene, P. G. M. Wuts in "Protective Groups in Organic Synthesis", Wiley, 1991 and 1999.

vii) by converting the hydroxy compound of general formula (VIII) into a primary amine of formula (IX)

The conversion of the alcohol function into an amine is carried out in a two-step process by Mitsunobu activation analogously to ii). The amine of general formula (XII) is obtained by reaction with phthalimide and subsequent release of the amine with hydrazine or methylamine.

Alternatively the hydroxy function may also be converted into a leaving group such as for example a mesylate, tosylate, iodide or the like, according to methods known from the literature. The amine of general formula (XII) is obtained by subsequent nucleophilic substitution with a compound selected for example from among lithium, sodium or potassium azide, sodium or potassium phthalimide, 4-methoxybenzylamine, benzylamine, 2,4-dimethoxybenzylamine, dibenzylamine, potassium or sodium cyanide, and subsequent reduction of the nitrogen-containing group thus introduced using standard procedures.

viii) by nucleophilic substitution with phthalimide

The conversion of the alcohol (VIII) into the corresponding phthalimide derivative (IX) may be carried out under Mitsunubo conditions, conveniently in an inert solvent or mixture of solvents such as for example tetrahydrofuran, dioxane, benzene, toluene, xylene, acetonitrile in the presence of phosphines such as for example triphenylphosphine, tributylphosphine with dialkylazodicarboxylates such as for example diethylazodicarboxylate, diisopropylazodicarboxylate, di(tert.-butyl)azodicarboxylate, for example at a temperature of −50 to 200° C., but preferably between −20 and 150° C.

ix) Tandem reaction consisting of nucleophilic epoxide opening followed by cyclisation to form compounds of general formula (VIII)

The preparation of oxazolidinones (VIII) from benzylcarbamates of general formula (X) and epoxides of general formula (VIII) is carried out in a solvent or mixture of solvents such as tetrahydrofuran, 1,4-dioxane, n-hexane or diethyl ether, for example, at temperatures between −100° C. and 150° C., but preferably at temperatures between −100° C. and 100° C.

x) by carbamoylation of an amine (II) with chlorobenzylformic acid esters

The acylation is conveniently carried out in a solvent such as methylene chloride, chloroform, carbon tetrachloride, ether, tetrahydrofuran, dioxane, benzene, toluene, acetonitrile, dimethylformamide or sulpholane, optionally in the presence of an inorganic or organic base at temperatures between −20 and 200° C., but preferably at temperatures between −10 and 160° C.

Other methods of amide coupling are described for example in P. D. Bailey, I. D. Collier, K. M. Morgan in "Comprehensive Functional Group Interconversions", Vol. 5, page 257ff., Pergamon 1995 or in the Houben-Weyl supplementary volume 22, Thieme Verlag, 2003 and the literature mentioned therein.

(b) The components of general formula

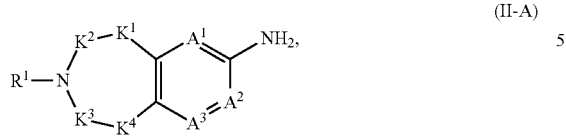

(II-A)

wherein $A^1$, $A^2$, $A^3$, $K^1$, $K^2$, $K^3$, $K^4$ and $R^1$ are defined as mentioned in embodiment 1, and which may optionally be protected at any amino, hydroxy, carboxy or thiol groups present by the usual protective groups, such as for example those described in T. W. Greene, P. G. M. Wuts in "Protective Groups in Organic Synthesis", and the protective groups of which can be cleaved in a manner known from the literature in the course of the synthesis sequence to form compounds of formula (I), are known from the literature, or the synthesis thereof is described in the embodiments by way of example, or they may for example be prepared by methods of synthesis known from the literature or analogously to methods of synthesis known from the literature as described for example in EP1818330, WO07/009,963, WO07/003,536, DE4429079, U.S. Pat. No. 4,490,369, DE3515864, U.S. Pat. No. 5,175,157, DE1921861, WO85/00808 or in G. Bobowski et al., J. Heterocyclic Chem. 16, 1525, 1979 or in P. D. Johnson et al., Bioorg. Med. Chem. Lett 2003, 4197.

For example, a compound of general formula (II-A), wherein $A^1$, $A^2$, $A^3$, $K^1$, $K^2$, $K^3$, $K^4$ and $R^1$ are defined as in embodiment 1, may be prepared by reduction of the nitro group of a compound of general formula (II-B)

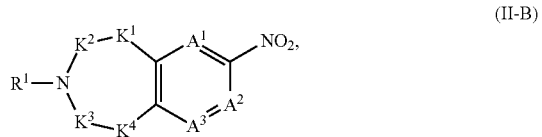

(II-B)

wherein $A^1$, $A^2$, $A^3$, $K^1$, $K^2$, $K^3$, $K^4$ and $R^1$ are defined as in embodiment 1, as follows.

The reduction of the nitro group is for example conveniently carried out in a solvent or mixture of solvents such as water, aqueous ammonium chloride solution, hydrochloric acid, sulphuric acid, phosphoric acid, formic acid, acetic acid, acetic anhydride with base metals such as iron, zinc, tin or sulphur compounds such as ammonium sulphide, sodium sulphide or sodium dithionite or by catalytic hydrogenation with hydrogen, for example at a pressure between 0.5 and 100 bar, but preferably between 1 and 50 bar, or with hydrazine as reducing agent, conveniently in the presence of a catalyst such as for example Raney nickel, palladium charcoal, platinum oxide, platinum on mineral fibres or rhodium, or with complex hydrides such as lithium aluminium hydride, sodium borohydride, sodium cyanoborohydride, diisobutylaluminium hydride, conveniently in a solvent or mixture of solvents such as water, methanol, ethanol, isopropanol, pentane, hexane, cyclohexane, heptane, benzene, toluene, xylene, ethyl acetate, methylpropionate, glycol, glycoldimethylether, diethyleneglycoldimethylether, dioxane, tetrahydrofuran, N-methylpyrrolidinone, or N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C.

In the reactions described above any reactive groups present such as hydroxy, carboxy, amino, alkylamino or imino groups may be protected during the reaction by conventional protecting groups which are cleaved again after the reaction. For example a suitable protecting group for a hydroxy group may be the methoxy, benzyloxy, trimethylsilyl, acetyl, benzoyl, tert.butyl, trityl, benzyl or tetrahydropyranyl group, suitable protecting groups for a carboxyl group might be the trimethylsilyl, methyl, ethyl, tert.butyl, benzyl or tetrahydropyranyl group, and suitable protecting groups for an amino, alkylamino or imino group might be the acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, the phthalyl group, suitable protecting groups for an ethynyl group might be the trimethylsilyl, diphenylmethylsilyl, tert.butyldimethylsilyl or a 1-hydroxy-1-methyl-ethyl group.

Other protective groups and their cleaving are described in T. W. Greene, P. G. M. Wuts, "Protective Groups in Organic Synthesis", Wiley, 1991 and 1999.

Any protective group used may optionally subsequently be cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved hydrogenolytically, for example, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, preferably, however, 1 to 5 bar.

A methoxybenzyl group may also be cleaved in the presence of an oxidising agent such as cerium(IV)ammonium nitrate in a solvent such as methylene chloride, acetonitrile or acetonitrile/water at temperatures of between 0 and 50° C., but preferably at ambient temperature.

A methoxy group is expediently cleaved in the presence of boron tribromide in a solvent such as methylene chloride at temperatures between −35 and −25° C.

A 2,4-dimethoxybenzyl group is preferably cleaved in trifluoroacetic acid in the presence of anisole.

A tert.butyl or tert.butyloxycarbonyl group is preferably cleaved by treating with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

An allyloxycarbonyl group is cleaved by treating with a catalytic amount of tetrakis-(triphenylphosphine)-palladium (0), preferably in a solvent such as tetrahydrofuran and preferably in the presence of an excess of a base such as morpholine or 1,3-dimedone at temperatures between 0 and 100° C., preferably at ambient temperature and under an inert gas, or by treating with a catalytic amount of tris-(triphenylphosphine)-rhodium(I)chloride in a solvent such as aqueous ethanol and optionally in the presence of a base such as 1,4-diazabicyclo[2.2.2]octane at temperatures between 20 and 70° C.

Moreover the compounds of general formula (I) obtained may be resolved into their enantiomers and/or diastereomers.

Thus, for example, the compounds of general formula (I) obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by chromatographic column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides may be a (+)- or (−)-menthyloxycarbonyl, for example.

Furthermore, the compounds of formula (I) may be converted into the salts thereof, particularly for pharmaceutical use into the physiologically acceptable salts thereof with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula (I) contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

As already mentioned, the compounds of general formula (I) as well as the tautomers, the enantiomers, the diastereomers and the physiologically acceptable salts thereof have valuable pharmacological properties, particularly an antithrombotic activity, which is preferably based on an effect on thrombin or factor Xa, for example on a thrombin-inhibiting or factor Xa-inhibiting activity, on a prolonging effect on the aPTT time and on an inhibiting effect on related serine proteases such as e.g. Urokinase, factor VIIa, factor IX, factor XI and factor XII.

The compounds listed in the experimental section may be investigated for their effect on the inhibition of factor Xa as follows:

Method:

Enzyme-kinetic measurement with chromogenic substrate. The quantity of p-nitroaniline (pNA) released from the colourless chromogenic substrate by human factor Xa is determined photometrically at 405 nm. It is proportional to the activity of the enzyme used. The inhibition of the enzyme activity by the test substance (in relation to the solvent control) is determined at various concentrations of test substance and from this the $IC_{50}$ is calculated, as the concentration which inhibits the factor Xa used by 50%.

Material:

Tris(hydroxymethyl)-aminomethane buffer (100 mMol) and sodium chloride (150 mMol), pH 8.0 plus 1 mg/ml Human Albumin Fraction V, protease-free. Factor Xa (Calbiochem), spec. Activity: 217 IU/mg, final concentration: 7 IU/ml for each reaction mixture Substrate S 2765 (Chromogenix), final concentration: 0.3 mM/l (1 KM) for each reaction mixture Test substance: final concentration 100, 30, 10, 3, 1, 0.3, 0.1, 0.03, 0.01, 0.003, 0.001 µMol/l Procedure:

10 µl of a 23,5-times concentrated starting solution of the test substance or solvent (control), 175 µl of TRIS/HSA buffer and 25 µl of a 65.8 U/L Factor Xa working solution are incubated for 10 minutes at 37° C. After the addition of 25 µl of S 2765 working solution (2.82 mMol/l) the sample is measured in a photometer (SpectraMax 250) at 405 nm for 600 seconds at 37° C.

Evaluation:
1. Determining the maximum increase (deltaOD/minutes) over 21 measuring points.
2. Determining the (% inhibition based on the solvent control.
3. Plotting a dosage/activity curve (% inhibition vs substance concentration).
4. Determining the $IC_{50}$ by interpolating the X-value (substance concentration) of the dosage/activity curve at Y=50% inhibition.

All the compounds tested have an $IC_{50}$ value of less than 100 µmol/L.

The compounds prepared according to the invention are generally well tolerated.

In view of their pharmacological properties the new compounds and the physiologically acceptable salts thereof are suitable for the prevention and treatment of venous and arterial thrombotic diseases, such as for example the prevention and treatment of deep leg vein thrombosis, thrombophlebitis, for preventing reocclusions after bypass operations or angioplasty (PT(C)A), and occlusion in peripheral arterial diseases, and for preventing and treating pulmonary embolism, disseminated intravascular coagulation and severe sepsis, for preventing and treating DVT in patients with exacerbation of COPD, for treating ulcerative colitis, for treating and preventing coronary thrombosis, for preventing stroke and the occlusion of shunts.

In addition, the compounds according to the invention are suitable for antithrombotic support in thrombolytic treatment, such as for example with alteplase, reteplase, tenecteplase, staphylokinase or streptokinase, for preventing long-term restenosis after PT(C)A, for the prevention and treatment of ischaemic events in patients with all forms of coronary heart disease, for preventing metastasis and the growth of tumours and inflammatory processes, e.g. in the treatment of pulmonary fibrosis, for preventing and treating rheumatoid arthritis, for preventing and treating fibrin-dependent tissue adhesions and/or the formation of scar tissue and for promoting wound healing processes.

The compounds specified may also be used as anticoagulants in connection with the preparation, storage, fractionation or use of whole blood or in invasive therapies, e.g. for coating prostheses, artificial heart valves and catheters for reducing the risk of thrombosis.

In view of their pharmacological properties the new compounds and the physiologically acceptable salts thereof are also suitable for treating Alzheimer's and Parkinson's disease. One rationale for this can be seen for example in the following findings, from which it can be concluded that thrombin inhibitors or factor Xa inhibitors, by inhibiting thrombin formation or activity, could be valuable drugs for treating Alzheimer's and Parkinson's disease. Clinical and experimental studies indicate that neurotoxic mechanisms, for example the inflammation that accompanies the activation of proteases of the clotting cascade, are involved in the dying off of neurones following brain damage. Various studies indicate an involvement of thrombin in neurodegenerative processes, e.g. following a stroke, repeated bypass operations or traumatic brain injury. An increased thrombin activity was able to be detected for example some days after peripoheral nerve damage. It was also shown that thrombin causes neurite retraction and glia proliferation, and apoptosis in primary cultures of neurones and neuroblastoma cells (for an overview see: *Neurobiol. Aging*, 2004, 25(6), 783-793). In addition, various in vitro studies on the brains of patients with Alzheimer's disease indicate that thrombin plays a part in the pathogenesis of this disease (*Neurosci. Lett.*, 1992, 146, 152-54). An accumulation of immunoreactive thrombin has been detected in neurite plaques in the brains of Alzheimer's patients. It was demonstrated in vitro that thrombin also plays a part in the regulation and stimulation of the production of Amyloid Precursor Protein (APP) as well as in the cleaving of APP into fragments which can be detected in the amyloid plaques in the brains of Alzheimer's patients. It has also been shown that thrombin-induced microglial activation in vivo leads to the degeneration of nigral dopaminergic neurones. These findings lead one to conclude that microglial activation, triggered by endogenous substance(s) such as thrombin, for example, are involved in the neuropathological process of the cell death of dopaminergic neurones, such as occurs in patients with Parkinson's disease (*J. Neurosci.*, 2003, 23, 5877-86).

The new compounds and the physiologically acceptable salts thereof can also be used for the prevention and treatment of arterial vascular diseases in combination therapy with lipid-lowering active substances such as HMG-CoA reductase inhibitors and vasodilators, particularly ACE inhibitors, angiotensin II antagonists, renin inhibitors, f3-receptor antagonists, α-receptor antagonists, diuretics, Ca-channel blockers, or stimulators of soluble guanylate cyclase.

By increasing the antithrombotic activity the new compounds and the physiologically acceptable salts thereof can also be used in combination therapy with other anticoagulants such as, for example, unfractionated heparin, low-molecular heparin, fondaparinux or direct thrombin inhibitors, for example recombinant hirudine or "active-site" thrombin inhibitors.

The new compounds and the physiologically acceptable salts thereof may be used therapeutically in conjunction with acetylsalicylic acid, with inhibitors of platelet aggregation such as fibrinogen receptor antagonists (e.g. abciximab, eptifibatide, tirofiban, roxifiban), with physiological activators and inhibitors of the clotting system and the recombinant analogues thereof (e.g. Protein C, TFPI, antithrombin), with inhibitors of ADP-induced aggregation (e.g. clopidogrel, prasugrel, ticlopidine), with $P_2T$ receptor antagonists (e.g. cangrelor) or with combined thromboxane receptor antagonists/synthetase inhibitors (e.g. terbogrel).

The dosage required to achieve such an effect is appropriately 0.01 to 3 mg/kg, preferably 0.03 to 1.0 mg/kg by intravenous route, and 0.03 to 30 mg/kg, preferably 0.1 to 10 mg/kg by oral route, in each case administered 1 to 4 times a day.

For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The new compounds and the physiologically acceptable salts thereof may be used therapeutically in conjunction with acetylsalicylic acid, with inhibitors of platelet aggregation such as fibrinogen receptor antagonists (e.g. Abciximab, eptifibatide, tirofiban, roxifiban), with physiological activators and inhibitors of the clotting system and the recombinant analogues thereof (e.g. Protein C, TFPI, antithrombin), with inhibitors of ADP-induced aggregation (e.g. clopidogrel, ticlopidine), with $P_2T$ receptor antagonists (e.g. cangrelor) or with combined thromboxane receptor antagonists/synthetase inhibitors (e.g. Terbogrel).

EXPERIMENTAL SECTION

The following Examples are intended to illustrate the invention, without restricting its scope.

As a rule, melting points and/or IR, UV, $^1$H-NMR and/or mass spectra have been obtained for the compounds prepared. Unless otherwise stated, $R_f$ values were obtained using ready-made silica gel 60 $F_{254}$ TLC plates (E. Merck, Darmstadt, Item no. 1.05714) without chamber saturation. The $R_f$ values obtained under the name Alox were determined using ready-made aluminium oxide 60 $F_{254}$ TLC plates (E. Merck, Darmstadt, Item no. 1.05713) without chamber saturation. The $R_f$ values obtained under the name Reversed-phase-8 were determined using ready-made RP-8 $F_{254s}$ TLC plates (E. Merck, Darmstadt, Item no. 1.15684) without chamber saturation. The ratios given for the eluants refer to units by volume of the solvents in question. Chromatographic purification was done using silica gel supplied by Messrs Millipore (MATREX™, 35-70 µm). If the configuration is not specified in detail, it is unclear whether the compound in question is a pure stereoisomer or a mixture of enantiomer and diastereomer.

In the descriptions of the experiments the following abbreviations are used:

Boc tert.-butoxycarbonyl
DCC N,N'-dicyclohexylcarbodiimide
DIPEA N-ethyl-diisopropylamine
DMSO dimethylsulphoxide
DMF N,N-dimethylformamide
DPPA diphenylphosphorylazide
sat. saturated
i. vac. in vacuo
conc. concentrated
NMM N-methyl-morpholine NMP N-methyl-pyrrolidin-2-on o ortho PfTU O-pentafluorophenyl-N,N,N',N'-tetramethyluronium-hexafluorophosphate PPA propanephosphonic acid cycloanhydride quant. quantitative $R_f$ retention factor $R_t$ retention time rac. racemic TBTU O-(benzotriazol-1-yl)-N,N,N',N'-tetramethyluronium tetrafluoroborate TEA triethylamine TFA trifluoroacetic acid THF tetrahydrofuran tert. tertiary Σ yield over all the steps carried out analogously The HPLC data for all the other Examples were obtained under the following conditions:

Method A

Waters Alliance 2695, Waters Micromass ZQ mass spectrometer with diode array detector 2996.

The mobile phase used was:

A: water with 0.13% TFA

B: acetonitrile

| time in min | % A | % B | flow rate in ml/min |
|---|---|---|---|
| 0.00 | 95 | 5 | 3.50 |
| 0.18 | 95 | 5 | 3.50 |
| 2.00 | 2 | 98 | 3.50 |
| 2.20 | 2 | 98 | 3.50 |
| 2.30 | 95 | 5 | 3.50 |
| 2.50 | 95 | 5 | 3.50 |
| 2.60 | 95 | 5 | 0.10 |

The stationary phase used was a Varian MS 100 C18 column, 3 μm, 4.6 mm×30 mm.

The diode array detection was carried out in the wavelength range from 210-380 nm.

Method B

Waters Alliance 2695, Waters ZMD with diode array detector 2996.

The mobile phase used was:

A: water with 0.13% TFA

B: acetonitrile with 0.10% TFA

| time in min | % A | % B | flow rate in ml/min |
|---|---|---|---|
| 0.00 | 95 | 5 | 1.00 |
| 0.75 | 95 | 5 | 1.00 |
| 5.25 | 2 | 98 | 1.00 |
| 5.75 | 2 | 98 | 1.00 |
| 6.05 | 95 | 5 | 1.00 |
| 6.55 | 95 | 5 | 1.00 |

The stationary phase used was a Varian MS 100 C18 column, 3 μm, 4.6 mm×50 mm.

The diode array detection was carried out in the wavelength range from 210-300 nm.

EXAMPLE 1

(S)-5-chloro-thiophene-2-carboxylic acid-[3-(2-methyl-1,2,3,4-tetrahydro-isoquinolin-6-yl)-2-oxo-oxazolidin-5-ylmethyl]-amide (as the trifluoroacetate salt)

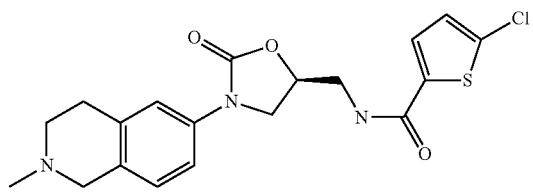 [SMILES: CN1CCc2cc(N3C[C@H](CNC(=O)c4ccc(Cl)s4)OC3=O)ccc2C1]

(a) tert.butyl 6-benzyloxycarbonylamino-3,4-dihydro-1H-isoquinoline-2-carboxylate 5.0 g (20.1 mmol) tert.butyl 6-amino-3,4-dihydro-1H-isoquinoline-2-carboxylate are dissolved in 90 ml dichloromethane and at 0° C. combined with 4.3 ml (25.1 mmol) DIPEA. Then 3.7 ml (25.1 mmol) benzyl chloroformate are added dropwise within one hour. Then the mixture is heated to RT, stirred for 3 hours and then washed twice with water. The organic phase is dried on sodium sulphate and evaporated down i. vac.

$R_f$ value: 0.46 (silica gel; dichloromethane/ethanol=95:5)

$C_{22}H_{26}N_2O_6$ (382.45)

Mass spectrum: $(M+NH_4)^+=400$ (b) benzyl (1,2,3,4-tetrahydro-isoquinolin-6-yl)-carbamate (as the trifluoroacetate salt)

9.3 g (24.3 mmol) tert.butyl 6-benzyloxycarbonylamino-3,4-dihydro-1H-isoquinoline-2-carboxylate are dissolved in 150 ml dichloromethane and combined with 18 ml trifluoroacetic acid. After two hours the reaction mixture is washed with sat. sodium hydrogen carbonate solution, the organic phase is dried on sodium sulphate and concentrated i. vac. The precipitate thus formed is filtered and dried.

$R_f$ value: 0.10 (silica gel; dichloromethane/ethanol/conc. Ammonia=95:5:0.1)

$C_{17}H_{18}N_2O_2 \times CF_3CO_2H$ (282.35)

Mass spectrum: $(M+H)^+=476$ (c) benzyl (2-methyl-1,2,3,4-tetrahydro-isoquinolin-6-yl)-carbamate 1.5 g (3.8 mmol) benzyl (1,2,3,4-tetrahydro-isoquinolin-6-yl)-carbamate (as the trifluoroacetate salt) are suspended in 8 ml of methanol and adjusted to pH 6 with acetic acid. 0.6 ml (8.5 mmol) formalin solution (37% in water) are added and the mixture is stirred for 30 minutes at RT. Then a total of 1.8 g (8.5 mmol) sodium triacetoxyborohydride are added batchwise and the mixture is stirred for two hours. The reaction mixture is poured onto sat. sodium hydrogen carbonate solution and extracted three times with ethyl acetate. The combined organic phases are dried on sodium sulphate and evaporated to dryness i.vac.

$R_t$ value: 1.12 min (Method A)

$C_{18}H_{20}N_2O_2$ (296.36)

Mass spectrum: $(M+H)^+=297$

(d) (S)-5-hydroxymethyl-3-(2-methyl-1,2,3,4-tetrahydro-isoquinolin-6-yl)-oxazolidin-2-one 600 mg (2 mmol) benzyl (2-methyl-1,2,3,4-tetrahydro-isoquinolin-6-yl)-carbamate are dissolved in 20 ml THF and at −65° C. slowly combined with 2.7 ml n-butyl lithium solution (1.6 M in n-hexane). The mixture is stirred for 30 minutes at this temperature and then 330 µl (2.3 mmol) oxiranylmethyl (R)-butyrate are added dropwise thereto. The mixture is left to warm up to RT and stirred for three days. The mixture is then applied to silica gel and purified by chromatography on silica gel (eluant dichloromethane/methanol 9:1).

$R_f$ value: 0.16 (silica gel; dichloromethane/methanol 9:1)
$C_{14}H_{18}N_2O_3$ (262.30)
Mass spectrum: $(M+H)^+=263$

(e) 3-(2-methyl-1,2,3,4-tetrahydro-isoquinolin-6-yl)-2-oxo-oxazolidin-5-ylmethyl(S)-methanesulphonate 279 mg (1.1 mmol) (S)-5-hydroxymethyl-3-(2-methyl-1,2,3,4-tetrahydro-isoquinolin-6-yl)-oxazolidin-2-one are dissolved in 5 ml dichloromethane and combined with 600 µl (4.3 mmol) TEA. At 0° C., 250 µl (3.2 mmol) methanesulphonyl chloride are added dropwise. The mixture is heated to RT and stirred for 5 hours. Then it is mixed with water and extracted three times with ethyl acetate. The combined organic phases are dried on sodium sulphate and evaporated to dryness i.vac.

$R_t$ value: 0.76 min (Method A)
$C_{15}H_{20}N_2O_5S$ (340.40)

(f) (S)-5-azidomethyl-3-(2-methyl-1,2,3,4-tetrahydro-isoquinolin-6-yl)-oxazolidin-2-one 359 mg (1.1 mmol) 3-(2-methyl-1,2,3,4-tetrahydro-isoquinolin-6-yl)-2-oxo-oxazolidin-5-ylmethyl(S)-methanesulphonate are dissolved in 2 ml DMF and combined with 223 mg (3.5 mmol) sodium azide. The mixture is stirred at 50° C. for 16 hours. Then it is mixed with water and extracted three times with ethyl acetate. The combined organic phases are dried on sodium sulphate and evaporated to dryness i.vac.

$R_t$ value: 0.83 min (Method A)
$C_{14}H_{17}N_5O_2$ (287.32)
Mass spectrum: $(M+H)^+=288$

(g) (S)-5-aminomethyl-3-(2-methyl-1,2,3,4-tetrahydro-isoquinolin-6-yl)-oxazolidin-2-one 184 mg (0.6 mmol) (S)-5-azidomethyl-3-(2-methyl-1,2,3,4-tetrahydro-isoquinolin-6-yl)-oxazolidin-2-one are dissolved in a mixture of 2 ml THF and 10 ml of methanol, combined with 50 mg palladium/charcoal (5%) and hydrogenated for two hours at 3 bar hydrogen pressure. The catalyst is filtered off and the filtrate is evaporated to dryness i. vac.

$R_t$ value: 0.24 min (Method A)
$C_{14}H_{19}N_3O_2$ (261.32)
Mass spectrum: $(M+H)^+=262$

(h) (S)-5-chloro-thiophene-2-carboxylic acid-[3-(2-methyl-1,2,3,4-tetrahydro-isoquinolin-6-yl)-2-oxo-oxazolidin-5-ylmethyl]-amide (as the trifluoroacetate salt)

74 mg (0.5 mmol) 5-chlorothiophene-2-carboxylic acid are dissolved in 1 ml DMF, combined with 212 µl (1.38 mmol) NMM and 175 mg (0.5 mmol) HATU and stirred for 15 minutes at RT. Then 120 mg (0.5 mmol) (S)-5-aminomethyl-3-(2-methyl-1,2,3,4-tetrahydro-isoquinolin-6-yl)-oxazolidin-2-one, dissolved in 0.5 ml DMF, are added dropwise. The mixture is stirred for 16 hours at RT. Then it is acidified with TFA and purified by reversed-phase chromatography.

$R_t$ value: 1.08 min (Method A)
$C_{19}H_{20}ClN_3O_3S \times CF_3CO_2H$ (405.91)
Mass spectrum: $(M+H)^+=406/408$ (chlorine isotopes)

The following compounds may be synthesised from derivatives that are known from the literature or that may be prepared analogously to methods of synthesis known from the literature, analogously to the above synthesis steps or analogously to methods of synthesis known from the literature:

| Structural formula No. Name | Mass peak(s) | $R_f$ value or $R_t$ |
|---|---|---|
| 2 (S)-5-chloro-thiophene-2-carboxylic acid-[3-(3-methyl-2,3,4,5-tetrahydro-1H-benzo[d]azepin-7-yl)-2-oxo-oxazolidin-5-ylmethyl]-amide (as the trifluoroacetate salt) | $(M+H)^+=$ 420/422 (chlorine isotopes) | 3.95 min (Method B) |
| 3 (S)-5-chloro-thiophene-2-carboxylic acid-[3-(2-methyl-1,2,3,4-tetrahydro-isoquinolin-7-yl)-2-oxo-oxazolidin-5-ylmethyl]-amide (as the trifluoroacetate salt) | $(M+H)^+=$ 406/408 (chlorine isotopes) | 1.08 min (Method A) |

-continued

| No. | Structural formula Name | Mass peak(s) | $R_f$ value or $R_t$ |
|---|---|---|---|

4

(S)-5-chloro-thiophene-2-carboxylic acid-[3-(3,5-dimethyl-2,3,4,5-tetrahydro-1H-benzo[d]azepin-7-yl)-2-oxo-oxazolidin-5-ylmethyl]-amide

5

(S)-5-chloro-thiophene-2-carboxylic acid-[3-(3.5.5-trimethyl-2,3,4,5-tetrahydro-1H-benzo[d]azepin-7-yl)-2-oxo-oxazolidin-5-ylmethyl]-amide

6

(S)-5-chloro-thiophene-2-carboxylic acid-[3-(1,2-dimethyl-1,2,3,4-tetrahydro-isoquinolin-6-yl)-2-oxo-oxazolidin-5-ylmethyl]-amide

7

(S)-5-chloro-thiophene-2-carboxylic acid-[3-(2,3-dimethyl-1,2,3,4-tetrahydro-isoquinolin-6-yl)-2-oxo-oxazolidin-5-ylmethyl]-amide

8

(S)-5-chloro-thiophene-2-carboxylic acid-[3-(2,4-dimethyl-1,2,3,4-tetrahydro-isoquinolin-6-yl)-2-oxo-oxazolidin-5-ylmethyl]-amide

| No. | Structural formula Name | Mass peak(s) | $R_f$-value or $R_t$ |
|---|---|---|---|

9

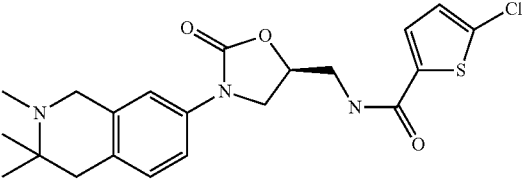

(S)-5-chloro-thiophene-2-carboxylic acid-[3-(2.3.3-trimethyl-1,2,3,4-tetrahydro-isoquinolin-6-yl)-2-oxo-oxazolidin-5-ylmethyl]-amide

10

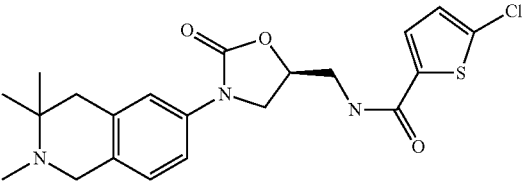 [SMILES: CN1Cc2ccc(N3C[C@H](CNC(=O)c4ccc(Cl)s4)OC3=O)cc2CC1(C)C]

(S)-5-chloro-thiophene-2-carboxylic acid-[3-(2.3.3-methyl-1,2,3,4-tetrahydro-isoquinolin-7-yl)-2-oxo-oxazolidin-5-ylmethyl]-amide

11

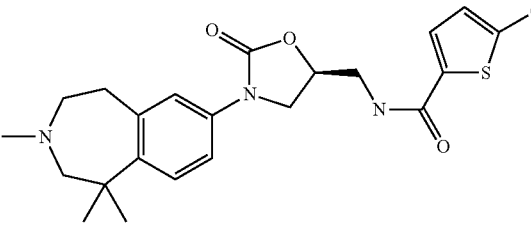

(S)-5-chloro-thiophene-2-carboxylic acid-[3-(1,1,3-trimethyl-2,3,4,5-tetrahydro-1H-benzo[d]azepin-7-yl)-2-oxo-oxazolidin-5-ylmethyl]-amide

12

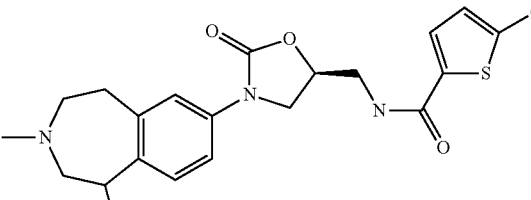

(S)-5-chloro-thiophene-2-carboxylic acid-[3-(1,3-dimethyl-2,3,4,5-tetrahydro-1H-benzo[d]azepin-7-yl)-2-oxo-oxazolidin-5-ylmethyl]-amide

13

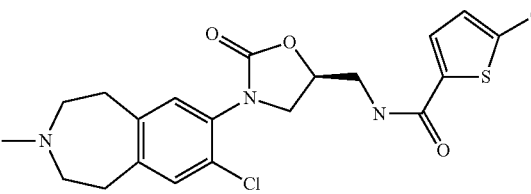

(S)-5-chloro-thiophene-2-carboxylic acid-[3-(8-chloro-3-methyl-2,3,4,5-tetrahydro-1H-benzo[d]azepin-7-yl)-2-oxo-oxazolidin-5-ylmethyl]-amide -continued

| Structural formula No. Name | Mass peak(s) | $R_f$ value or $R_t$ |
|---|---|---|

14

(S)-5-chloro-thiophene-2-carboxylic acid-[2-oxo-3-(1.1,2-trimethyl-1,2,3,4-tetrahydro-isoquinolin-6-yl)-oxazolidin-5-ylmethyl]-amide

15

(S)-5-chloro-thiophene-2-carboxylic acid-[2-oxo-3-(2.4.4-trimethyl-1,2,3,4-tetrahydro-isoquinolin-6-yl)-oxazolidin-5-ylmethyl]-amide

16

(S)-5-chloro-thiophene-2-carboxylic acid-[3-(7-chloro-2-methyl-1,2,3,4-tetrahydro-isoquinolin-6-yl)-oxazolidin-5-ylmethyl]-amide

17

(S)-5-chloro-thiophene-2-carboxylic acid-[3-(5-fluoro-2-methyl-1,2,3,4-tetrahydro-isoquinolin-6-yl)-oxazolidin-5-ylmethyl]-amide The Examples that follow describe the preparation of some pharmaceutical formulations which contain as active substance any desired compound of general formula I:

EXAMPLE A

Dry Ampoule Containing 75 mg of Active Substance Per 10 ml

Composition:

| Active substance | 75.0 mg |
|---|---|
| Mannitol | 50.0 mg |
| water for injections | ad 10.0 ml |

Preparation:

Active substance and mannitol are dissolved in water. After packaging the solution is freeze-dried. To produce the solution ready for use for injections, the product is dissolved in water.

EXAMPLE B

Dry Ampoule Containing 35 mq of Active Substance Per 2 ml

Composition:

| Active substance | 35.0 mg |
|---|---|
| Mannitol | 100.0 mg |
| water for injections | ad 2.0 ml |

Preparation:

Active substance and mannitol are dissolved in water. After packaging, the solution is freeze-dried.

To produce the solution ready for use for injections, the product is dissolved in water.

EXAMPLE C

Tablet Containing 50 mq of Active Substance

Composition:

| (1) Active substance | 50.0 mg |
|---|---|
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

EXAMPLE D

Tablet Containing 350 mq of Active Substance

Composition:

| (1) Active substance | 350.0 mg |
|---|---|
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

EXAMPLE E

Capsules Containing 50 mq of Active Substance

Composition:

| (1) Active substance | 50.0 mg |
|---|---|
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatine capsules in a capsule filling machine.

EXAMPLE F

Capsules Containing 350 mg of Active Substance

Composition:

| (1) Active substance | 350.0 mg |
|---|---|
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing.

This powder mixture is packed into size 0 hard gelatine capsules in a capsule filling machine.

EXAMPLE G

Suppositories Containing 100 mg of Active Substance

1 Suppository Contains:

| Active substance | 100.0 mg |
|---|---|
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation:

The polyethyleneglycol is melted together with polyethylenesorbitan monostearate. At 40° C. the ground active substance is homogeneously dispersed in the melt. It is cooled to 38° C. and poured into slightly chilled suppository moulds.

The invention claimed is:
1. Compounds of formula (I),

(I)

wherein
D denotes a substituted bicyclic ring system of formula (II)

(II)

, wherein $K^1$ and $K^4$
each independently of one another denote a —$CH_2$, —$CHR^{2a}$—or a —$CR^{2b}R^{2c}$ group represent, and wherein $R^{2a}/R^{2b}/R^{2c}$
each independently of one another denote a methyl group, or two groups $R^{2b}/R^{2c}$ together with the cyclic carbon atom may form a cyclopropyl ring, and $K^2$ and $K^3$
each independently of one another denote a —$CH_2$, —$CHR^{6a}$ or —$CR^{6b}R^{6c}$—group, wherein $R^{6a}/R^{6b}/R^{6c}$
each independently of one another denote a methyl group,
or two groups $R^{6b}/R^{6c}$ together with the cyclic carbon atom may form a cyclopropyl ring, and $R^1$ denotes a hydrogen atom or a $C_{1-3}$-alkyl, or $C_{3-6}$-cycloalkyl group, and $A^1$ denotes $CR^9$,
$A^2$ denotes $CR^{10}$,
$A^3$ denotes $CR^{11}$,
while $R^9$, $R^{10}$ and $R^{11}$ each independently of one another denote a hydrogen, fluorine or chlorine atom, or a methyl, $CF_3$, cyano, methoxy, $CF_3O$, $CHF_2O$, $CH_2FO$—group, and Y denotes a carbonyl group, and
A denotes an oxygen atom, and
$R^3$, $R^4$ and $R^5$ each represent a hydrogen atom, and
B denotes a thiophene ring according to formula (III),

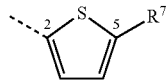

(III)

which is bound to the carbonyl group in formula (I) via the 2 position and which is substituted in the 5 position by $R^7$, where $R^7$ denotes a chlorine or bromine atom, or an ethynyl group, the tautomers, the enantiomers, the diastereomers, the mixtures thereof and the salts thereof.

2. Physiologically acceptable salts of the compounds according to claim 1.

3. A pharmaceutical composition comprising a compound according to claim 1 or a physiologically acceptable salt thereof, optionally in addition to one or more inert carriers and/or diluents.

4. Process for preparing a pharmaceutical composition, characterised in that a compound according to claim 1 or a physiologically acceptable salt thereof is incorporated in one or more inert carriers and/or diluents by a non-chemical method.

5. A compound of formula (I) according to claim 1, selected from a group consisting of:

(S)-5-chloro-thiophene-2-carboxylic acid-[3-(3-methyl-2,3,4,5-tetrahydro-1H-benzo[d]azepin-7-yl)-2-oxo-oxazolidin-5-ylmethyl1]-amide, (S)-5-chloro-thiophene-2-carboxylic acid-[3-(3,5-dimethyl-2,3,4,5-tetrahydro-1H-benzo[d]azepin-7-yl)-2-oxo-oxazolidin-5-ylmethyl1]-amide, (S)-5-chloro-thiophene-2-carboxylic acid-[3-(3.5.5-trimethyl-2,3,4,5-tetrahydro-1H-benzo[d]azepin-7-yl)-2-oxo-oxazolidin-5-ylmethyl1]-amide, (S)-5 -chloro-thiophene-2-carboxylic acid-[3-(1,1,3-trimethyl-2,3,4,5-tetrahydro-1H-benzo[d]azepin-7-yl)-2-oxo-oxazolidin-5-ylmethyl1]-amide, (S)-5 -chloro-thiophene-2-carboxylic acid-[3-(1,3-dimethyl-2,3,4,5-tetrahydro-1H-benzo[d]azepin-7-yl)-2-oxo-oxazolidin-5-ylmethyl1]-amide, (S)-5 -chloro-thiophene-2-carboxylic acid-[3-(8-chloro-3-methyl-2,3,4,5-tetrahydro-1H-benzo[d]azepin-7-yl)-2-oxo-oxazolidin-5-ylmethyl1]-amide, a tautomer, an enantiomer, a diastereomer, the mixtures thereof and the salts thereof.

* * * * *